United States Patent
Xia et al.

(10) Patent No.: US 11,529,262 B2
(45) Date of Patent: Dec. 20, 2022

(54) MICRO-NEGATIVE PRESSURE FOAM DRESSING AND MANUFACTURING METHOD THEREOF

(71) Applicant: Zhende Medical Co., Ltd., Shaoxing (CN)

(72) Inventors: Feng Xia, Shaoxing (CN); Jianguo Lu, Shaoxing (CN)

(73) Assignee: Zhende Medical Co., Ltd., Shaoxing (CN)

( * ) Notice: Subject to any disclaimer, the term of this patent is extended or adjusted under 35 U.S.C. 154(b) by 0 days.

(21) Appl. No.: 17/215,361

(22) Filed: Mar. 29, 2021

(65) Prior Publication Data

US 2021/0212863 A1 Jul. 15, 2021

Related U.S. Application Data

(63) Continuation of application No. PCT/CN2019/121091, filed on Nov. 27, 2019.

(30) Foreign Application Priority Data

Apr. 29, 2019 (CN) .......................... 201910356112.3

(51) Int. Cl.
*A61F 13/00* (2006.01)
*A61M 1/00* (2006.01)
*A61F 13/02* (2006.01)

(52) U.S. Cl.
CPC .... *A61F 13/00068* (2013.01); *A61F 13/0206* (2013.01); *A61M 1/90* (2021.05); *A61M 2205/364* (2013.01)

(58) Field of Classification Search
CPC .. A61M 1/90; A61F 13/00068; A61F 13/0206
See application file for complete search history.

(56) References Cited

U.S. PATENT DOCUMENTS 6,479,724 B1* 11/2002 Areskoug ........... A61F 13/0256
602/41
2004/0199231 A1* 10/2004 Yim ....................... A61F 7/034
607/114
(Continued)

FOREIGN PATENT DOCUMENTS

CN 1389186 A 1/2003
CN 102202619 A 9/2011
(Continued)

OTHER PUBLICATIONS

"European Application No. 19863993.2, Communication pursuant to Article 94(3) EPC dated Feb. 9, 2021", (dated Feb. 9, 2021), 5 pgs.
(Continued)

*Primary Examiner* — Tatyana Zalukaeva
*Assistant Examiner* — Nhu Q. Tran
(74) *Attorney, Agent, or Firm* — Schwegman Lundberg & Woessner, P.A.

(57) ABSTRACT

A micro-negative pressure foam dressing and a manufacturing method thereof is disclosed, the dressing comprises a exothermic agent layer, an isolation component covering on the exothermic agent layer, an elastic memory piece disposed under the exothermic agent layer, a liquid absorbing negative pressure pad disposed under the elastic memory piece, a contact layer disposed under the liquid absorbing negative pressure pad, a sealing film disposed between the liquid absorbing negative pressure pad and the contact layer, and a bottom release film disposed under the contact layer; and in this invention, heat generated by a exothermic agent layer causes an elastic memory piece to expand downward to compress a foam layer, and after the heat dissipates completely, a micro-negative pressure is generated since a sealed environment is formed by a sealing film, a contact (Continued)

layer and a wound surface without a need for the VSD negative pressure technology.

9 Claims, 1 Drawing Sheet

(56) References Cited

U.S. PATENT DOCUMENTS

| | | | | |
|---|---|---|---|---|
| 2010/0121286 A1* | 5/2010 | Locke | ............... | A61F 13/00068 |
| | | | | 602/53 |
| 2010/0241089 A1* | 9/2010 | Uchiyama | ............... | A61F 7/034 |
| | | | | 604/291 |
| 2010/0286600 A1* | 11/2010 | Bommannan | ......... | A61M 37/00 |
| | | | | 514/357 |
| 2013/0261541 A1* | 10/2013 | Johannison | ......... | A61M 1/0023 |
| | | | | 604/73 |
| 2015/0174291 A1* | 6/2015 | Zimnitsky | .............. | A61K 31/14 |
| | | | | 604/290 |
| 2017/0173316 A1* | 6/2017 | Syrek | .................... | A61M 37/00 |
| 2017/0231813 A1* | 8/2017 | Huang | ................. | A45D 44/002 |
| | | | | 607/109 |
| 2017/0360602 A1* | 12/2017 | Nishioka | ................... | A61F 7/03 |
| 2018/0353336 A1* | 12/2018 | Locke | ............... | A61F 13/15203 |
| 2020/0121509 A1* | 4/2020 | Locke | ...................... | A61M 1/90 |
| 2020/0337906 A1* | 10/2020 | Long | ................... | A61F 13/0209 |

FOREIGN PATENT DOCUMENTS

| | | |
|---|---|---|
| CN | 102755664 A | 10/2012 |
| CN | 203169655 U | 9/2013 |
| CN | 205163393 U | 4/2016 |
| CN | 109938920 A | 6/2019 |
| CN | 209916384 U | 1/2020 |
| KR | 20080062248 A | 7/2008 |
| WO | WO-0185248 A1 | 11/2001 |
| WO | WO-2009002260 A1 | 12/2008 |
| WO | WO-2012156655 A1 | 11/2012 |
| WO | WO-2014134073 A1 | 9/2014 |
| WO | WO-2020220659 A1 | 11/2020 |

OTHER PUBLICATIONS

"International Application No. PCT/CN2019/121091, International Search Report dated Feb. 14, 2020", (Feb. 14, 2020), 6 pgs.

* cited by examiner

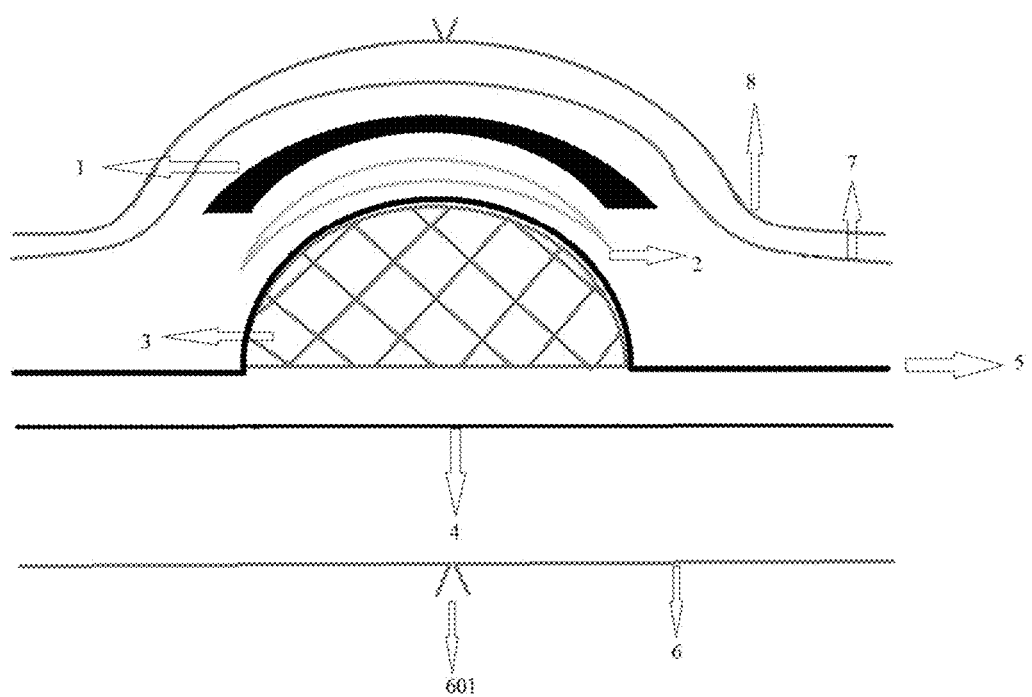

MICRO-NEGATIVE PRESSURE FOAM DRESSING AND MANUFACTURING METHOD THEREOF

CLAIM OF PRIORITY

This application is a continuation application of International Application No. PCT/CN2019/121091, filed 27 Nov. 2019, which claims the benefit of priority to Chinese Application No. 201910356112.3, filed 29 Apr. 2019, the benefit of priority of each of which is claimed herein, and which applications are hereby incorporated herein by reference in their entirety.

TECHNICAL FIELD

The invention relates to a field of dressings, in particular to a micro-negative pressure foam dressing.

BACKGROUND ART

Negative pressure drainage technologies are widely used in clinical practice and it can absorb the human body's bleeding, exudate, liquefied necrotic tissue fragments and liquefied substances such as pus into the outside of the wound surface. And thus, a generation of neovascularization and a rapid growth of granulation tissue can be facilitated, thereby accelerating a wound healing and relieving pain of patients. However, the commonly used VSD negative pressure technologies in clinic at present pose defects of complicated operation, high cost, lack of portability and the like, which can be solved by the present invention.

SUMMARY OF THE INVENTION

In order to solve the defects of the prior art, the invention aims to provide a micro-negative pressure foam dressing and a manufacturing method thereof, in which foam dressing heat generated by a exothermic agent layer causes an elastic memory piece to expand downward to compress a foam layer, and after the heat dissipates completely, a micro-negative pressure is generated since a sealed environment is formed by a sealing film, a contact layer and a wound surface, which is simple to operate, low in cost and portable.

In order to achieve the above object, the invention adopts the following technical scheme:

A micro-negative pressure foam dressing comprises a exothermic agent layer, an isolation component covering on the exothermic agent layer, an elastic memory piece disposed under the exothermic agent layer, a liquid absorbing negative pressure pad disposed under the elastic memory piece, a contact layer disposed under the liquid absorbing negative pressure pad, a sealing film disposed between the liquid absorbing negative pressure pad and the contact layer, and a bottom release film disposed under the contact layer.

In the aforementioned micro-negative pressure foam dressing, the liquid absorbing negative pressure pad is a foam layer.

In the aforementioned micro-negative pressure foam dressing, the micro-negative pressure foam dressing comprises a soft silicone foam layer and a polyurethane foam layer.

In the aforementioned micro-negative pressure foam dressing, the formula of the exothermic agent layer is as follows in mass ratio: iron powder:activated carbon:table salt:vermiculite:water=$(40\pm10):(15\pm10):(5\pm3):(10\pm3):(5\pm3)$.

In the aforementioned micro-negative pressure foam dressing, the isolation component consists of a non-woven fabric disposed on the exothermic agent layer and a top release film covering on the non-woven fabric.

In the aforementioned micro-negative pressure foam dressing, the elastic memory piece comprises a memory resin piece, a PP piece and a PU piece.

In the aforementioned micro-negative pressure foam dressing, the contact layer is a punched silicon gel layer.

In the aforementioned micro-negative pressure foam dressing, the sealing film is a polyurethane film.

In the aforementioned micro-negative pressure foam dressing, the bottom release film is provided with an opening.

A manufacturing method of a micro-negative pressure foam dressing, which comprises the following steps:

Step 1, spreading a silicon gel film on a horizontal plane, and stamping and punching it by a mechanical punching mode;

Step 2, spreading the punched silicon gel film on a composite board, and placing a hemispherical liquid absorbing negative pressure pad on an upper surface;

Step 3, covering a cut-out sealing film on a liquid absorbing negative pressure pad, and compounding the silicon gel layer and the sealing film using an annular pressure roller to obtain a semi-finished product;

Step 4, transferring the semi-finished product into a vacuum operation table;

Step 5, placing a elastic memory piece above the sealing film, and coating an exothermic agent layer over the elastic memory piece;

Step 6, covering a cut-out non-woven fabric coated with glue over the exothermic agent layer, and pressing the non-woven fabric to bond with the sealing film together with the exothermic agent layer;

Step 7, placing a cut-out release film at the positions above and below the product respectively, and compounding them with an annular pressure roller;

Step 8, taking out the product, die-cutting and shaping it followed by packaging and sterilizing.

The invention has the advantages that:

In this invention, heat generated by an exothermic agent layer causes an elastic memory piece to expand downward to compress a foam layer, and after the heat dissipates completely, a micro-negative pressure is generated since a sealed environment is formed by a sealing film, a contact layer and a wound surface without a need for the VSD negative pressure technology, which is simple to operate, simple in structure, low in cost, small in volume and portable;

The micro-negative pressure lasts for a long time which ranges from 48 hours to 72 hours;

The product of the invention has no glue in the contact layer with the wound surface, no sensitization and no wound adhesion, and can relieve pain of patients.

BRIEF DESCRIPTION OF DRAWINGS

FIG. 1 is a schematic structural diagram of an embodiment of the present invention;

MEANING OF REFERENCE SIGNS IN THE FIGURE 1 exothermic agent layer, 2 elastic memory piece, 3 liquid absorbing negative pressure pad, 4 contact layer, 5 sealing film, 6 bottom release film, 601 opening, 7 non-woven fabric, 8 top release film.

DETAILED DESCRIPTION OF EMBODIMENTS

The present invention will be described in detail below with reference to the drawings and specific embodiments.

A micro-negative pressure foam dressing comprises a exothermic agent layer 1, an isolation component covering on the exothermic agent layer 1, an elastic memory piece 2 disposed under the exothermic agent layer 1, a liquid absorbing negative pressure pad 3 disposed under the elastic memory piece 2, a contact layer 4 disposed under the liquid absorbing negative pressure pad 3, a sealing film 5 disposed between the liquid absorbing negative pressure pad 3 and the contact layer 4, and a bottom release film 6 disposed under the contact layer 4.

As an embodiment, the liquid absorbing negative pressure pad 3 is a foam layer; and material of the foam layer can be selected form soft silicone, polyurethane or gelatin sponge, and if soft silicone is selected, this layer is both a negative pressure layer and an absorption layer. It should be noted that the material of the absorbing negative pressure pad 3 is not limited.

As a preference, the material of the foam layer is selected to be soft silicone foam with advantages: soft texture, low mechanical pressure on wound, large liquid absorption, which can absorb 6-8 times of its own weight of the exudate, readily available raw materials, and good compounding strength with the contact layer 4, but with disadvantages of 1.7 times price compared with polyurethane foam.

As another preference, the material of the foam layer is selected to be polyurethane foam with advantages: low price, soft texture, liquid absorption of 4-6 times of its own weight, readily available raw materials, but with disadvantages that a compounding strength with contact layer 4 is not strong.

As another preference, the material of the foam layer is selected to be gelatin sponge with advantages: large liquid absorption and good compounding strength with contact layer 4, but with disadvantages that the mechanical strength is larger, the texture is coarser and the price is higher compared with the above two sponges.

The formula of the exothermic agent layer 1 is as follows in mass ratio: iron powder:activated carbon:salt:vermiculite:water=(40±10):(15±10):(5±3):(10±3):(5±3), and with the ratio of activated carbon and vermiculite lowering the heat dissipation speed will be accelerated, so that the elastic memory piece 2 deforms and shrinks violently and the negative pressure is obvious; as a preference, the optimal formula of the exothermic agent layer 1 is as follows in mass ratio: iron powder:activated carbon:salt:vermiculite:water=40:15:5:10:5.

The isolation component consists of a non-woven fabric 7 disposed on the exothermic agent layer 1 and a top release film 8 covering on the non-woven fabric 7. As an embodiment, the top release film 8 and the bottom release film 6 can be selected from one of PET release film, OPP release film, PEK release paper, CCK release paper and glassine release paper.

As an example, the materials that the elastic memory piece 2 can be selected from include: memory resin, PP, PU.

As a preference, the contact layer 4 is a perforated silicon gel layer, and the perforated silicon gel layer is the contact layer 4 in which the silicon gel adheres to the skin in such a way that the contact area with the skin is increased. In this way, the contact can be made to adhere with the skin without using glue, thus avoiding a secondary injury to the wound caused by removing an application.

As an example, the sealing film 5 is a polyurethane film, and the material is not limited, for which a polyethylene film, polypropylene film, and Nylon film can be selected.

The bottom release film 6 is provided with an opening 601, on which a small opening needs to be made after the top release film 8 is removed, followed by laying for 5 min and completely removing the bottom release film 6, so that the heating layer contacts with air for 5 min to generate enough heat absorbed by the elastic memory piece 2 to expand and deform, and thus after the dressing is sticked to the wound, the elastic memory piece 2 dissipates the heat and shrinks to generate a negative pressure.

Usage: remove the upper release film of the product, make a small opening in the bottom release film layer 6 through the opening 601, lay for 1 min, remove the bottom release film layer 6, and stick the micro-negative pressure foam application to the wound surface.

Principle of use: remove the release film above the product, make the air contact the exothermic agent to generate heat to make the elastic memory piece 2 expand downward to press the foam layer, and then stick the product on the wound surface. After the heat dissipates completely, the elastic memory piece 2 will be cooled and shrink to rebound to the original state, but a composite layer of the polyurethane film layer and the perforated silicon gel layer forms a sealed environment with the wound surface, thus generating a micro-negative pressure.

Specific Manufacturing Process:

Step 1: spread the silicon gel film on a horizontal plane, and stamp and punch it by a mechanical punching mode;

Step 2: spread the punched silicon gel film on a composite board, and place a hemispherical liquid absorbing negative pressure pad 3 on the upper surface;

Step 3: cover the cut-out sealing film 5 on the liquid absorbing negative pressure pad 3, and compound the silicon gel layer and the sealing film 5 using an annular pressure roller to obtain a semi-finished product;

Step 4: transfer the semi-finished product into a vacuum operation table;

Step 5: place the elastic memory piece 2 above the sealing film 5, and coat the exothermic agent layer 1 over the elastic memory piece 2;

Step 6: cover the cut-out non-woven fabric 7 coated with a small amount of glue over the exothermic agent layer, and slightly press the non-woven fabric 7 to bond with the sealing film 5 together with the exothermic agent layer 1;

Step 7: place the cut-out release film at the positions above and below the product respectively, and compound them with an annular pressure roller;

Step 8: take out the product, die-cut and shape it followed by packaging and sterilizing.

According to the above manufacturing method, 72 products were produced with 72 ulcer patient volunteers called in;

Carry out contact tests on these 72 ulcer patients, of which 1 patient was lost, and the following is the data recorded on the diary card for 71 people:

| Description | Number/Person |
| --- | --- |
| The negative pressure of the described product disappeared after 24 hours of use | 0 |
| The negative pressure of the | 13 |

| Description | Number/Person |
| --- | --- |
| described product disappeared after 48 hours of use | |
| The negative pressure of the described product disappeared after 72 hours of use | 58 |
| The negative pressure of the described product disappeared after 96 hours of use | 0 |

The results show that the micro-negative pressure lasts for a long time which ranges from 48 hours to 72 hours.

The invention provides a micro-negative pressure foam dressing, in which heat generated by a exothermic agent layer 1 causes an elastic memory piece 2 to expand downward to compress a foam layer, and after the heat dissipates completely, a micro-negative pressure is generated in a sealed environment formed by a sealing film 5, a contact layer 4 and a wound surface, which is simple to operate, low in cost and portable.

The above shows and describes the basic principles, main features and advantages of the present invention. It should be understood by those skilled in the art that the above-mentioned embodiments do not limit the present invention in any form, and all technical solutions obtained by equivalent substitution or equivalent transformation fall within the scope of protection of the present invention.

What is claimed is:

1. A micro-negative pressure foam dressing, comprising an exothermic agent layer,
   an isolation component covering on the exothermic agent layer,
   an elastic memory piece disposed under the exothermic agent layer,
   a liquid absorbing negative pressure pad disposed under the elastic memory piece,
   a contact layer disposed under the liquid absorbing negative pressure pad,
   a sealing film disposed between the liquid absorbing negative pressure pad and the contact layer, and
   a bottom release film disposed under the contact layer;
   the liquid absorbing negative pressure pad includes a foam layer;
   wherein when the release film is removed, air contacts the exothermic agent, heat generated by the exothermic agent layer causes the elastic memory piece to expand downward to compress the foam layer, and after the heat dissipates completely, a micro-negative pressure is generated in a sealed environment formed by the sealing film, the contact layer and a wound surface.

2. The micro-negative pressure foam dressing according to claim 1, wherein a material of the foam layer is a soft silicone foam or a polyurethane foam.

3. The micro-negative pressure foam dressing according to claim 1, wherein a formula of the exothermic agent layer is as follows in mass ratio: iron powder:activated carbon: table salt:vermiculite:water=(40±10):(15±10):(5±3):(10±3): (5±3).

4. The micro-negative pressure foam dressing according to claim 1, wherein the isolation component consists of a non-woven fabric disposed on the exothermic agent layer and a top release film covering on the non-woven fabric.

5. The micro-negative pressure foam dressing according to claim 1, wherein a material of the elastic memory piece is memory resin, PP piece, or PU.

6. The micro-negative pressure foam dressing according to claim 1, wherein the contact layer is a punched silicone gel layer.

7. The micro-negative pressure foam dressing according to claim 1, wherein the sealing film is a polyurethane film.

8. The micro-negative pressure foam dressing according to claim 1, wherein the bottom release film is provided with an opening.

9. A manufacturing method of a micro-negative pressure foam dressing, comprising the following steps:
   step 1, spreading a silicon gel film on a horizontal surface, and stamping and punching it by a mechanical punching mode;
   step 2, spreading the punched silicon gel film on a composite board, and placing a hemispherical liquid absorbing negative pressure pad on an upper surface;
   step 3, covering a cut-out sealing film on the liquid absorbing negative pressure pad, and compounding the silicon gel layer and the sealing film using an annular pressure roller to obtain a semi-finished product;
   step 4, transferring the semi-finished product into a vacuum operation table;
   step 5, placing an elastic memory piece above the sealing film, and coating an exothermic agent layer over the elastic memory piece;
   step 6, covering a cut-out non-woven fabric coated with glue over the exothermic agent layer, and pressing the non-woven fabric to bond with the sealing film together with the exothermic agent layer;
   step 7, placing a cut-out release film at the positions above and below the product respectively, and compounding them with an annular pressure roller;
   step 8, taking out the product, die-cutting and shaping, and packaging and sterilizing.

* * * * *